United States Patent
Komeda (12)

(10) Patent No.: US 6,274,340 B1
(45) Date of Patent: Aug. 14, 2001

(54) DNA SEQUENCES ENHANCING PROMOTER ACTIVITY

(75) Inventor: Toshihiro Komeda, Kanagawa (JP)

(73) Assignee: Kirin Beer Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/297,053

(22) PCT Filed: Aug. 28, 1998

(86) PCT No.: PCT/JP98/03848

§ 371 Date: Apr. 23, 1999

§ 102(e) Date: Apr. 23, 1999

(87) PCT Pub. No.: WO99/11779

PCT Pub. Date: Mar. 11, 1999

(30) Foreign Application Priority Data

Aug. 29, 1997 (JP) .................................................. 9-234995

(51) Int. Cl.[7] ...................................................... C12P 21/06
(52) U.S. Cl. ....................... 435/69.1; 435/440; 435/471; 435/320.1; 435/252.3; 435/254.11; 435/254.22; 536/24.1
(58) Field of Search ..................................... 435/69.1, 440, 435/471, 320.1, 252.3, 254.11, 254.22; 536/24.1

(56) References Cited

U.S. PATENT DOCUMENTS 6,001,590 * 12/1999 Komeda et al. .................... 435/69.1

FOREIGN PATENT DOCUMENTS 9-135694  5/1997 (JP) .
97/10345  3/1997 (WO) .
WO97/10345 * 3/1997 (WO) .

OTHER PUBLICATIONS

Sakai et al. Journal of Bacteriology, vol. 179(14): 4480–4485, Jul. 1997.*
Allen et al. Gene. vol. 162(1): 99–104, 1995.*
S.J. Allen et al., Isolation, sequence and overexpression of the gene encoding NAD–dependent formate dehydrogenase from the methylotrophic yeast *Candida methylica*, Gene, vol. 162, No. 1, pp. 99–104, (1995).
Yasuyoshi Sakai et al., Regulation of the Formate Dehydrogenase Gene, FDH1, in the Methylotrophic Yeast *Candida boidinii* and Growth Characteristics of an FDH1–Disrupted Strain on Methanol, Methylamine, and Choline, Journal of Bacteriology, vol. 179, No. 14, Jul. 1997, pp. 4480–4485.

* cited by examiner

*Primary Examiner*—Remy Yucel
(74) *Attorney, Agent, or Firm*—Foley & Lardner

(57) ABSTRACT

The present invention relates to a DNA comprising the nucleotide sequence shown in SEQ ID NO:1, or a DNA for enhancing promoter activity which comprises a nucleotide sequence having deletions, substitutions, additions or insertions of one or more nucleotides in the nucleotide sequence shown in SEQ ID NO:1; to a mutant promoter comprising one or more fragments of the DNA; to a recombinant expression vector comprising the mutant promoter together with a heterologous gene; to a transformant prepared by transforming a host cell with the vector; to a process for preparing an expression product, comprising culturing the transformant in a medium, and recovering the expression product of a heterologous gene from the obtained culture; and to a method for enhancing a promoter activity, characterized in that one or more fragments of the above-defined DNA are located at at least one position preceding, following or within a selective promoter in a forward or reverse direction.

11 Claims, 8 Drawing Sheets

FIG. 2

| | Plasmid | Acid phosphatase activity (%) | |
|---|---|---|---|
| | | ME medium | GF medium |
| 1478 ——————————— | pPUF1 | 100 | 100 |
| 1215 ————————— | pPUF15 | 101 | 99 |
| 1000 ——————— | pPUF24 | 93 | 99 |
| 839 ————— | pPUF44 | 85 | 94 |
| 819 ———— | pPUF819 | 63 | 94 |
| 801 ———— | pPUF801 | 36 | 94 |
| 779 ———— | pPUF779 | 27 | 91 |
| 756 ———— | pPUF56 | 25 | 92 |
| 690 ——— | pPUF54 | 23 | 91 |
| 668 ——— | pPUF668 | 18 | 90 |
| 642 ——— | pPUF642 | 18 | 85 |
| 622 ——— | pPUF622 | 14 | 21 |
| 602 ——— | pPUF602 | 14 | 21 |
| 403 —— | pPUF79 | 15 | 21 |
| 228 —— | pPUF308 | 14 | 18 |
| 194 — | pPUF194 | 13 | 20 |
| 161 — | pPUF161 | 4 | 5 |
| 115 — | pPUF310 | 4 | 3 |
| | Parent strain | 4 | 4 |

FIG. 5

When inserted into XhoI site in forward direction

DNA fragment prepared with synthetic oligonucleotides UA3 and UA3C

```
    5'
.....C TCGAGTTTACCACTATCCAATTAAAAATCCATGGATCAGACGGTAGCTTTACCACTATCCAATTAAAAA
.....GAGCTCAAATGGTGATAGGTTAATTTTTAGGTACCTAGTCTGCCATCGAAATGGTGATAGGTTAATTTT
                                                                        3'
```

Cleavable with XhoI

```
TCCATGGATCAGACGGTAG  TCGAG.....
AGGTACCTAGTCTGCCATC  AGCT C.....
```

Not cleavable with XhoI

SEQUENCE LISTING

```
<160> NUMBER OF SEQ ID NOS: 26

<210> SEQ ID NO 1
<211> LENGTH: 40
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 1
tttaccacta tccaattaaa atccatggat cagacggtag                              40

<210> SEQ ID NO 2
<211> LENGTH: 1478
<212> TYPE: DNA
<213> ORGANISM: Candida boidinii
```

-continued

```
<400> SEQUENCE: 2
gtcaacaaat caatcagcca atctaccaat caattaaaaa tacactgaag tgatatagtt      60
tagtctaatc aaagttgaat aaccccagac atggttgaaa tcttagaagc cacaaatatc     120
aacaggccaa atcggctctc ggagaatctt ttctggcttc cagtgtatgg gctgttacgc     180
tacactcagt aaactgcctc ctctctgcat ctccatcttc cccacatttt atgcactaaa     240
cgccatcgca atatttcact agacttacag aacctttcac aatattaact ctctgtctct     300
gatgtaatcg atacaattca attcaactaa ataccatgat aaactcaaat aattgaagga     360
ctccgattta tgcttatcca acacttatat ccacttgtat tcattaccgt gctgtcttcc     420
gtggatcaga ttgcctctgt ctccctattc gtcaaatggc agagcaatca gggaaaaagc     480
tgggttttta ctgaattcag tcaagtaatc ctgtcggact ttttaatatc tagctttcac     540
aaaaaccaac aacaacaacc gctaatccca tcaaacaatt aaacaattgt tacaattgtc     600
acaattcttg gatatacaat aattaaacat acgtacattc ttacatacat atagagtttg     660
aaatagatac attacccagt gtcatcgata ttatgccccg ccttttttcac ttgaaacaat     720 aactattatt actactatta ttatttctat tcatatatcc taaaaattat attaaaattg     780 gctctttttat gcaaaaaatg tacatttatg gtaatactag tcagatgtta taattatatc     840
tttaccacta tccaattaaa atccatggat cagacggtag ttttttatatc tgtaacatct     900 tactactacc actactacta ccactactac taccactact actaccacta ctactactga     960
taataaggta tactacattt tatcatacgt gaaatgtaac gcgtagatta aacatttttt    1020
taaaattact gatcagtact ttccacaata agcacttatt aatatgtgcc tctttaaaat    1080
tacttaattc ccttttacttt tcatttttac aaccgctttg gtatttaccc ccagagtgtt    1140
ttaattgcaa ttgaattctt attttaattt ccattacttt ctttgtacca taatgaaatt    1200
gccgagttgt ccctcctttg aatttaaatc attctctaat atttaacttt aattttaata    1260
ttttagttat ttatttgaat taaagtaaat tcaactaaaa attgaactat ttaaacacta    1320
tgatttcctt caattatatt aaaatcaatt tcatatttcc ttacttcttt ttgctttatt    1380
atacatcaat aactcaatta actcattgat tatttgaaaa aaaaaaacat ttattaactt    1440
aactccccga ttatatatta tattattgac tttacaaa                            1478

<210> SEQ ID NO 3
<211> LENGTH: 1030
<212> TYPE: DNA
<213> ORGANISM: Candida boidinii

<400> SEQUENCE: 3
tcaataagag tgtgattata tacaatcagc tggtgttaac taaatatagt tatgaaattt      60
caccgcgcgt ttggttcacg tttcagtacc aagaattgat aatattggca gcggttcagt     120
gcgtttgctg cttcacctcc cgcattctct agtccggatt ctctgtattc ccccttacat     180
tgctggccat tgctggccat tcctggcaag gtatatgcca ctactgtgcc tgatttcttt     240
cacgcctgcc ttaccatcat gtctcttctg tatatccgcc caaccggcag acatccgct     300 taccacgcag cccaccgcgt ttatgtgagc gtcttgacct cgtctccttc ccgtttgccc     360
ctgtcaaccg ccctcatcact caccacagcc cctgaaatat acaccggatc atccagaaat     420
tacggctgac acagcctctg gatcccaggc aggcattaag gcattacatc agatagcgac     480
caccatgact gtacccactt tagccacttt aaccactctg ctaccgctct tctctgtctt     540
ccagcttgtc gcattagcct gcgagtcttc ccactgagtt ccttctttct gtttctgttt     600
```

```
ctcccagtgt ctccgagttt acccacttgt tttcattctc gttgttgtct cttgtttgtt      660
caattaccac tcccacccat ttctctcat ttctctcta ttctttcctc ccagattctg        720
tatccgccat ttcattcatc attcattcac ttattcatcc ttcatcatcc attcattcat      780
tcatttaccc aattaacctt ccaatctatc aattcattaa tcaatcaacg cctttccctc      840
cgaacacttc actcaattcc tcttctgata cactcttcga caatcaacaa tcaaatataa      900
atcagtatat caatttagat tcgtatatct aagtctcttc tatatccata tttgatttgt      960
tctctttctg atcaactaga tttataacct agatagattt tataaattta atttaatata     1020
tattacaaaa                                                            1030
```

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 4

```
ctaccgtctg atccatggat tttaattgga tagtggtaaa                             40
```

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 5

```
cccctcgagg aaatagatac attacccagt gtc                                    33
```

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 6

```
cccctcgagt gtcatcgata ttatgccccg cc                                     32
```

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 7

```
cccctcgagg ccttttcac ttgaaacaat aactat                                  36
```

<210> SEQ ID NO 8
<211> LENGTH: 38
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 8 ccccctcgagt aatactagtc agatgttata attatatc                                    38

<210> SEQ ID NO 9
<211> LENGTH: 37
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 9 ccccctcgagt atctttacca ctatccaatt aaaatcc                                     37

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 10 ccccctcgagt aaaatccatg gatcagacgg tag                                         33

<210> SEQ ID NO 11
<211> LENGTH: 35
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 11 ccccctcgagt agttttttata tctgtaacat cttac                                      35

<210> SEQ ID NO 12
<211> LENGTH: 46
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 12 ccccctcgagt aaattcaact aaaaattgaa ctatttaaac actatg                           46

<210> SEQ ID NO 13
<211> LENGTH: 42
<212> TYPE: DNA
<213> ORGANISM: Artificial Sequence
<220> FEATURE:
<223> OTHER INFORMATION: Description of Artificial Sequence:
      Synthetic DNA
<400> SEQUENCE: 13 ccccctcgaga tgatttcctt caattatatt aaaatcaatt tc                               42

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence:
      Synthetic DNA
<400> SEQUENCE: 14
caatgagccg ttgaattgac gagtg                                                   25

<210> SEQ ID NO 15
<211> LENGTH: 35
<212> TYPE: DNA
<213> ORGANISM: Artificial Sequence
<220> FEATURE:
<223> OTHER INFORMATION: Description of Artificial Sequence:
      Synthetic DNA
<400> SEQUENCE: 15
cccctcgagt caacaaatca atcagccaat ctacc                          35

<210> SEQ ID NO 16
<211> LENGTH: 35
<212> TYPE: DNA
<213> ORGANISM: Artificial Sequence
<220> FEATURE:
<223> OTHER INFORMATION: Description of Artificial Sequence:
      Synthetic DNA
<400> SEQUENCE: 16
ccagatcttg ataataaggt atactacatt ttatc                          35

<210> SEQ ID NO 17
<211> LENGTH: 44
<212> TYPE: DNA
<213> ORGANISM: Artificial Sequence
<220> FEATURE:
<223> OTHER INFORMATION: Description of Artificial Sequence:
      Synthetic DNA
<400> SEQUENCE: 17
ccagatctag tagtagtggt agtagtagtg gtagtagtaa gatg                44

<210> SEQ ID NO 18
<211> LENGTH: 41
<212> TYPE: DNA
<213> ORGANISM: Artificial Sequence
<220> FEATURE:
<223> OTHER INFORMATION: Description of Artificial Sequence:
      Synthetic DNA
<400> SEQUENCE: 18
ccagatctag tagtaagatg ttacagatat aaaaactacc g                   41

<210> SEQ ID NO 19
<211> LENGTH: 37
<212> TYPE: DNA
<213> ORGANISM: Artificial Sequence
<220> FEATURE:
<223> OTHER INFORMATION: Description of Artificial Sequence:
      Synthetic DNA
<400> SEQUENCE: 19
ccagatctct accgtctgat ccatggattt taattgg                        37

<210> SEQ ID NO 20
<211> LENGTH: 41
<212> TYPE: DNA
<213> ORGANISM: Artificial Sequence
<220> FEATURE:
<223> OTHER INFORMATION: Description of Artificial Sequence:
      Synthetic DNA
<400> SEQUENCE: 20
ccagatcttt aattggatag tggtaaagat ataattataa c                   41

<210> SEQ ID NO 21
<211> LENGTH: 36
<212> TYPE: DNA
<213> ORGANISM: Artificial Sequence
<220> FEATURE:
<223> OTHER INFORMATION: Description of Artificial Sequence:

```
                Synthetic DNA
<400> SEQUENCE: 21
ccagatctat aattataaca tctgactagt attacc                              36

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence:
      Synthetic DNA
<400> SEQUENCE: 22
ccctcgaggc tgggttttta ctgaattcag tc                                  32

<210> SEQ ID NO 23
<211> LENGTH: 86
<212> TYPE: DNA
<213> ORGANISM: Artificial Sequence
<220> FEATURE:
<223> OTHER INFORMATION: Description of Artificial Sequence:
      Synthetic DNA
<400> SEQUENCE: 23
tcgagtttac cactatccaa ttaaaatcca tggatcagac ggtagcttta ccactatcca    60
attaaaatcc atggatcaga cggtag                                         86

<210> SEQ ID NO 24
<211> LENGTH: 86
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 24
tcgactaccg tctgatccat ggattttaat tggatagtgg taaagctacc gtctgatcca    60
tggattttaa ttggatagtg gtaaac                                         86

<210> SEQ ID NO 25
<211> LENGTH: 38
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 25
ttctcgagtc aataagagtg tgattatata caatcagc                            38

<210> SEQ ID NO 26
<211> LENGTH: 49
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 26
ttgcggccgc ttttgtaata tatattaaat taaatttata aaatctatc                49
```

DNA SEQUENCES ENHANCING PROMOTER ACTIVITY

TECHNICAL FIELD

The present invention relates to a promoter with a high transcriptional activity useful in high level expression of heterologous genes, to an expression vector carrying the promoter, to a transformant introduced with the expression vector, and to a method for producing a heterologous protein by culturing the transformant.

BACKGROUND ART

A methanol assimilating yeast, i.e. methylotrophic yeast, is able to grow on methanol as a sole carbon source. In the initial reaction of methanol metabolism by the methylotrophic yeast, formaldehyde and hydrogen peroxide are produced from methanol and oxygen by alcohol oxidase. The produced hydrogen peroxide is catabolized into water and oxygen by catalase. The formaldehyde is oxidized to carbon dioxide through the actions of formaldehyde dehydrogenase, S-formylglutathione hydrolase, and formate dehydrogenase. NADH formed upon these oxidations becomes an energy source of the yeast cell. Simultaneously, due to the action of dihydroxyacetone synthase, the formaldehyde condenses with xylulose-5-phosphate, and the condensate product is converted into glyceraldehyde-3-phosphate and dihydroxyacetone, which become components of the yeast cell via pentose phosphate cycle. When the methylotrophic yeast is cultured in the presence of methanol, the above-mentioned alcohol oxidase, dihydroxyacetone synthase and formate dehydrogenase are produced in an extremely large amount, reaching about 40% of the intracellular soluble proteins.

As described above, the methylotrophic yeast is considered to be a suitable host for expression system of heterologous genes in that it can be mass-cultured with inexpensive methanol and that it has a promoter for methanol-metabolizing enzyme with a strong transcriptional activity unfound in other yeasts.

*Candida boidinii* is a kind of methylotrophic yeast. Utilizing this yeast, methods for expressing a heterologous gene by using regulatory regions of alcohol oxidase gene and formate dehydrogenase gene have been studied (JP-A-5-344895, WO97/10345, etc.). In most cases of such an expression system, a heterologous gene is produced in a larger amount within a transformant having the chromosome into which a higher copy number of an expression vector has been integrated (Appl. Microbiol. Biotechnol., 42, 860–864 (1995); Proceedings of Annual Meeting of Japan Society for Bioscience, Biotechnology, and Agrochemistry, 1997, p. 257; and Proceedings of Annual Meeting of Society for Bioscience and Bioengineering, Japan, 1997, p. 314). Considering the stability of an expression vector within a transformant, it seems to be more desirable to achieve a high amount of expression at a low copy number, and there has been a demand for developing promoters with stronger transcriptional activity.

DISCLOSURE OF INVENTION

The present invention aims at providing a promoter with strong transcriptional activity useful in expressing heterologous genes, an expression vector carrying the promoter, a transformant into which the expression vector has been introduced, and a method for preparing a heterologous gene expression product by utilizing the transformant.

For solution of the above problem, The present inventor has conducted intensive studies on development of promoters with high transcriptional activity. As a result, the present inventor has now found that a DNA fragment prepared by adding nucleotides with a specific nucleotide sequence to the promoter DNA fragment that functions in the methylotrophic yeast *Candida boidinii,* was used as a promoter to efficiently express a heterologous gene downstream of the promoter. By this finding, the present invention has been accomplished.

Accordingly, the present invention provides a DNA for enhancing promoter activity which comprises the nucleotide sequence shown in SEQ ID NO:1, or the nucleotide sequence having deletions, substitutions, additions or insertions of one or more nucleotides in the nucleotide sequence shown in SEQ ID NO:1.

The present invention also provides a mutant promoter wherein one or more fragments of the above-defined DNA are located at at least one position preceding, following or within any promoter in a forward or reverse direction.

The present invention further provides a recombinant expression vector comprising the mutant promoter together with a heterologous gene. The heterologous gene as used herein refers to any gene that is a target of expression unlimited to specific one. Examples of the heterologous gene include genes for acid phosphatase, α-amylase, various interferons, erythropoietin, and granulocyte colony-stimulating factor. The heterologous genes useful in the present invention are not limited by the method for preparing them.

The present invention still further provides a transformant prepared by transforming a host cell with the vector.

The present invention still yet further provides a method for enhancing a promoter activity, characterized in that one or more fragments of the above-defined DNA are located at at least one position preceding, following or within any promoter in a forward or reverse direction.

Moreover, the present invention provides a process for preparing an expression product, comprising culturing the above defined transformant in a medium, and recovering the expression product of a heterologous gene from the obtained culture. Examples of the medium include a medium containing methanol as a carbon source, a medium containing methanol supplemented with glycerol, and a medium containing formic acid supplemented with any carbon and nitrogen sources.

Hereinafter, the present invention will be described in more detail.

In accomplishing the present invention, the present inventor has identified a region (hereinafter, referred to as "UAS sequence") requisite for a transcriptional activity of a formate dehydrogenase gene promoter (hereinafter, often abbreviated as "FDH promoter") of the methylotrophic yeast *Candida boidinii*. More specifically, the DNA of the present invention is an UAS sequence comprising the nucleotide sequence 841–880 of the formate dehydrogenase gene promoter from *Candida boidinii* having the nucleotide sequence shown in SEQ ID NO:2.

As used herein, "any promoter" refers to a DNA fragment exhibiting a transcriptional activity in a host cell, which is not limited to specific one. Therefore, any promoter (i.e., a promoter DNA fragment) useful in the present invention may be derived from any organisms as long as it has a transcriptional activity. Moreover, any promoter may partially include a mutation such as substitution, deletion, addition or insertion in a nucleotide sequence from the corresponding wild type promoter as long as it has a transcriptional activity. The location and the number of the substitution, deletion, addition or insertion are not limited to specific ones. As the promoter of the invention, a *Candida boidinii* formate dehydrogenase gene promoter (SEQ ID NO:2) and a *Candida boidinii* actin gene promoter (SEQ ID NO:3) are exemplified. For instance, even a DNA fragment having a deletion of the nucleotides 1–300 in the nucleotide sequence shown in SEQ ID NO:2 may also be included in any promoter of the present invention as long as it exhibits a transcriptional activity in *Candida boidinii*. The introduction of the mutation may be carried out by general genetic engineering techniques including restriction enzyme treatment, utilization of chemically synthesized DNA, PCR method, site-directed mutagenesis, and methods for producing deletion mutants using Exonuclease III.

The mutant promoter of the present invention can be prepared by locating the UAS sequence at any promoter DNA fragment as described above in either a forward direction or a reverse direction.

Locating the UAS sequence in a forward direction means locating (e.g., adding or inserting) a sequence homologous to the UAS sequence, i.e.,

5'-TTTACCACTATCCAATTAAAATCCATGGATCA-GACGGTAG-3' (SEQ ID NO:1), at the promoter DNA fragment in the same 5'→3' orientation as the orientation of the promoter DNA fragment. On the other hand, locating the UAS sequence in a reverse direction means locating (e.g., adding or inserting) a sequence complementary to the UAS sequence, i.e.,

5,-CTACCGTCTGATCCATGGATTTTAATTGGATAG-TGGTAAA-3, (SEQ ID NO:4), at the promoter DNA fragment in the same 5'→3' orientation as the orientation of the promoter DNA fragment.

The mutant promoter useful in the invention may be a promoter DNA fragment comprising a single UAS sequence or a plurality of, preferably not less than two consecutive UAS sequences. The nucleotide sequence(s) of the single UAS sequence or the plurality of UAS sequences may be located in either forward or reverse direction, or co-existently located in forward and reverse directions.

(1) The construction of a mutant promoter, (2) the construction of an expression vector, and (3) the construction and cultivation of a transformant using the expression vector can be carried out as described below.

(1) Construction of Mutant Promoter

The mutant promoter of the invention can be prepared by adding a chemically synthesized UAS sequence to a promoter DNA fragment. The promoter DNA fragment already identified as a promoter sequence is obtainable by general gene cloning techniques (for example, methods described in Molecular Cloning, Cold Spring Harbor Lab., 1989), PCR methods, methods for chemical synthesis, or the like.

The DNA fragment which exhibits a promoter activity in a host cell may be obtained by using a library prepared by cloning a low-molecular-weight DNA fragment resulting from cleavage with restriction enzymes or the like into a site upstream of a marker gene of a plasmid which comprises a DNA sequence having an ability to replicate autonomously in a host cell and a marker gene containing no promoter sequence. Exemplary marker genes are antibiotic resistant genes, for example G418 resistant gene, and auxotrophic complementary genes, for example URA3 and LEU2 genes. When a host cell is transformed with the prepared library DNA, a transformant containing the plasmid where the DNA fragment with the promoter activity is cloned into a site immediately upstream the marker gene can be selected by the corresponding marker. Thus, from the obtained transformant, total DNA can be extracted and transformed into *E. coli* whereby the DNA fragment with the promoter activity is isolated efficiently.

The UAS sequence can be introduced by using a restriction enzyme site(s) present in the promoter DNA fragment or a restriction enzyme site(s) artificially added to the promoter DNA fragment through general genetic engineering techniques. For example, there is a method in which specific restriction enzyme site(s) is(are) introduced in both ends of the UAS sequence; a sequence recognized by the same restriction enzyme(s) is introduced into any promoter; and the UAS sequence and the promoter are ligated with each other.

(2) Construction of Expression Vector

The thus-obtained mutant promoter is inserted into a suitable vector together with a structural gene for heterologous protein, a terminator, a selective marker gene, a homologous region and the like, whereby the resulting vector is used as a heterologous gene expression vector. Exemplary vectors are well known vectors including *E. coli* plasmid vectors, for example pBR, pUC and Bluescript series. The terminator, the selective marker gene, and the homologous region can appropriately be chosen by those skilled in the art as long as they are able to function in a host. As the terminator, terminators for actin and formate dehydrogenase genes are exemplified. Examples of the selective marker gene include antibiotic resistant genes, for example G418 resistant gene, and auxotropihic complementary genes such as URA3 and LEU2. The insertion of the above elements into a vector for forming an expression vector could readily be carried out by those skilled in the art based on Examples described below or common techniques.

(3) Construction and Cultivation of Transformant

The transformant of the present invention can be prepared by introducing the above-obtained recombinant expression vector into a suitable host cell.

Hosts useful in the invention are, but are not limited to, *E. coli, Bacillus subtilis,* yeast, or the like, preferably yeast, more preferably methylotrophic yeast (i.e., methanol assimilating yeast). A specific example thereof is *Candida boidinii*. Introduction of the plasmid into the host can be carried out by general methods used for transformation, e.g., protoplast method, lithium method, electroporation method, calcium method, etc.

The expression vector of the invention may be integrated into a host chromosomal DNA. Alternatively, the expression vector may be present in the form of a plasmid by using a vector having an autonomously replicating sequence capable of self-replication in the host cell. The copy number of a heterologous gene present in the host cell may be one or more.

The thus-obtained transformant is then cultured. From the obtained culture, a heterologous gene expression product is recovered, thereby obtaining a gene expression product of interest. As used herein, the "gene expression product is recovered" means extracting a gene expression product from the cultured cell, or collecting a supernatant from the culture, or purifying an expression product from a supernatant of the culture.

Since the above-described transformant can induce expression of a heterologous gene with methanol or formic acid, the following media are exemplified:

When the expression is induced with methanol, the medium can be used which contains, in addition to methanol as a carbon source, one or more nitrogen sources, for example yeast extract, trypton, meat extract, peptone, Casamino acid, and ammonium salts; and inorganic salts, for example phosphoric acid, sodium, potassium, magnesium, calcium, iron, copper, manganese, and cobalt. Optionally, the medium may further include trace nutrients such as various types of vitamins, amino acids and nucleotides, and sugar materials which do not inhibit the induction.

When the expression is induced with formic acid, the medium can be used which contains, in addition to formic acid, one or more carbon sources, for example glucose and glycerol; one or more nitrogen sources, for example yeast extract, trypton, meat extract, peptone, Casamino acid, and ammonium salts; inorganic salts, for example phosphoric acid, sodium, potassium, magnesium, calcium, iron, copper, manganese, and cobalt; and optionally trace nutrients, for example various types of vitamins, amino acids and nucleotides, and sugar materials which do not inhibit the induction.

The pH of the medium is preferably in the range of 5 to 8. The temperature of cultivation is normally 15–45° C., preferably around 28° C. The cultivation can be conducted in either batchwise or continuous manner for a period of about 24 to 1000 hours under standing, shaking, agitating or aerating conditions.

At the end of the cultivation, a gene expression product can be recovered from a culture by using common protein purification processes, etc. For example, where the gene expression product is produced intracellularly in a transformant cell, it can be extracted according to any common method by subjecting the cell to sonication, grinding, disruption under pressure, or the like. When necessary, a protease inhibitor may be added. Where a gene expression product is produced in the supernatant of a culture, the culture solution may be used as such. The obtained solution can be filtrated and subsequently solids are removed from the filtrate by centrifugation, thereby obtaining a crude protein solution. When necessary, nucleic acids may be removed by protamine treatment, etc.

From the crude protein solution, a target protein can be isolated and purified by a combination of purification techniques such as salting-out, solvent precipitation, dialysis, ultrafiltration, gel electrophoresis, ion exchange chromatography, gel filtration chromatography, reversed phase chromatography, and affinity chromatography.

BRIEF DESCRIPTION OF DRAWINGS

FIG. 2 shows acid phosphatase activities expressed under the control of upstream-deleted-type FDH promoters.

FIG. 5 shows the chemically synthesized DNA fragment comprising a sequence corresponding to SEQ ID NO:1 which is regarded as the UAS sequence, as well as the way of inserting the DNA fragment at XhoI site.

BEST MODE FOR CARRYING OUT THE INVENTION

The following examples will illustrate the subject matter of the present invention in more detail, but they are not intended to limit any technical scope of the invention.

EXAMPLE 1

In the present example, modified FDH promoters, in which the upstream region of *Candida boidinii* FDH promoter has partially been deleted, were prepared in order to identify a region necessary for a function of the FDH promoter by determining the activity of the acid phosphatase from the yeast *Saccharomyces cerevisiae* under the control of the upstream-deleted-type FDH promoters.

(1-1) Preparation of Acid Phosphatase Expression Plasmid

Figure 1:
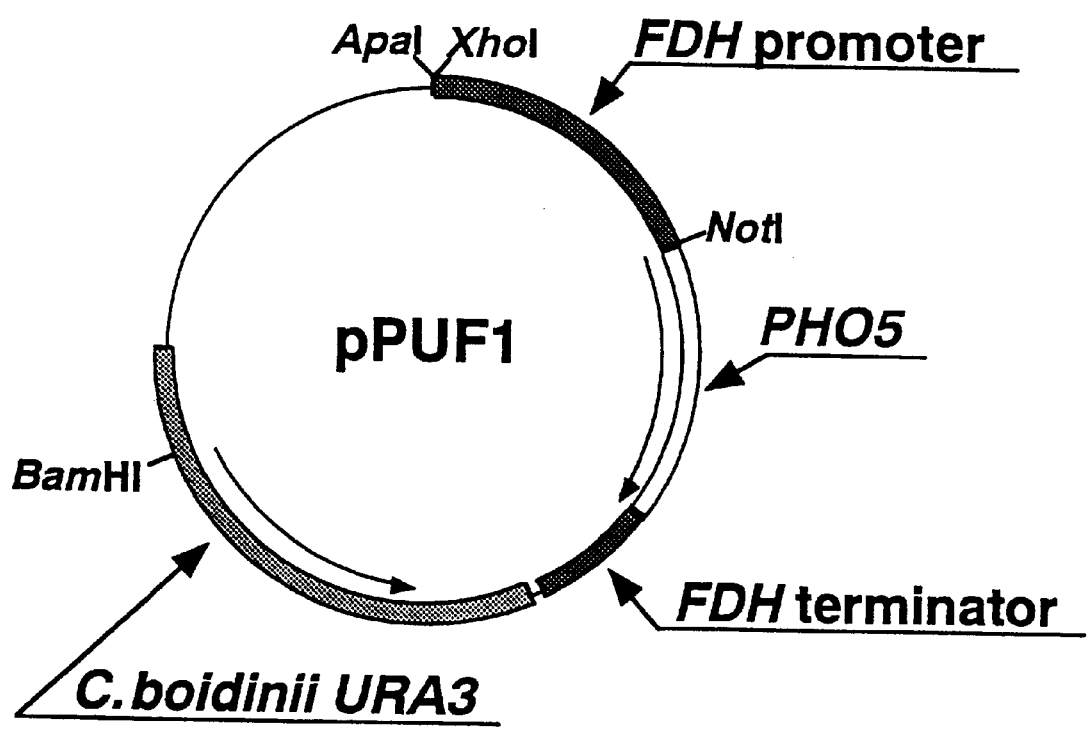
FIG. 1 shows the structure of plasmid pPUF1.

The acid phosphatase expression plasmid pPUF1 containing FDH promoter/terminator and URA3 gene as a marker gene (FIG. 1) was prepared according to the method described in WO97/10345. *Candida boidinii* strain KST2515 ura3 was used as a host strain. Plasmid pPUF1 can easily be obtained according to the method described in WO97/10345. The FDH promoter/terminator, the URA3 gene, and the PHO5 gene may be obtained by chemical synthesis based on the sequences described in WO97/10345, Sakai Y. et al., J. Ferment. Bioeng., 73, 255–260 (1992), and Arima, K. et al., Nucleic Acids Res., 11, 1657 (1983), respectively. Although *Candida boidini* strain KST2515 was used in the present example, the ura3 strain can easily be obtained by using other *Candida boidinii* strain such as IFO 10035 according to a known method (Sakai Y. et al., J. Bacteriol., 173, 7458 (1991)).

(1-2) Construction of PHO5 Expression Plasmids Under the Control of Upstream-Deleted-Type FDH Promoter Modified FDH promoters, in which the upstream region of the FDH promoter has partially been deleted, were prepared with Kilo-Sequence Deletion Kit (Takara Shuzo Co., Ltd.) and PCR. Plasmid pPUF1 was cleaved at ApaI and XhoI sites and treated with Kilo-Sequence Deletion Kit to obtain the PHO5 expression plasmids pPUF15, pPUF24, pPUF44, pPUF54, pPUF56, pPUF79, pPUF308, and pPUF310, which plasmids are under the control of the upstream-deleted-type FDH promoters. Using these plasmids as templates together with Dye Primer Cycle Sequencing Kit (Perkin-Elmer Co.), nucleotide sequences were determined, whereby it was confirmed that plasmids pPUF15, pPUF24, pPUF44, pPUF54, pPUF56, pPUF79, pPUF308 and pPUF310 had FDH promoter regions of 1215bp, 1000bp, 839bp, 690bp, 756bp, 403bp, 228bp and 115bp, respectively.

To prepare the upstream-deleted-type FDH promoters by PCR, the following oligonucleotides were synthesized:
PF819; CCCCTCGAGGAAATAGATACATTAC-CCAGTGTC (SEQ ID NO:5)
PF801; CCCCTCGAGTGTCATCGATATTATGCCCCGCC (SEQ ID NO:6)
PF779; CCCCTCGAGGCCTTTTTCACTTGAAA-CAATAACTAT (SEQ ID NO:7)

PF668; CCCCTCGAGTAATACTAGTCAGATGT-TATAATTATATC (SEQ ID NO:8)
PF642; CCCCTCGAGTATCTTTACCACTATC-CAATTAAAATCC (SEQ ID NO:9)
PF622; CCCCTCGAGTAAAATCCATGGATCA-GACGGTAG (SEQ ID NO:10)
PF602; CCCCTCGAGTAGTTTTTATATCTGTAA-CATCTTAC (SEQ ID NO:11)
PF194; CCCCTCGAGTAAATTCAACTAAAAAT-TGAACTATTTAAACACTATG (SEQ ID NO:12)
PF161; CCCCTCGAGATGATTTCCTTCAAT-TATATTAAAATCAATTTC (SEQ ID NO:13)
PRV3; CAATGAGCCGTTGAATTGACGAGTG (SEQ ID NO:14)

Using the oligonucleotide PRV3 and any one of the oligonuleotides PF819, PF801, PF779, PF668, PF642, PF622, PF602, PF194 and PF161 together with pPUF1 as a template, PCR was carried out (20 cycles of: 94° C. for 30 sec.; 55° C. for 1 min.; and 72° C. for 1 min.). Each of the amplified DNA fragments was cloned into pT7Blue T-Vector (Novagen, Inc.), from which a restriction fragment XhoI-NotI was cut out and then inserted into XhoI-NotI of pPUF1. PHO5 expression plasmids having:

the promoter region of 819 bp from primer PF819;
the promoter region of 801 bp from primer PF801;
the promoter region of 779 bp from primer PF779;
the promoter region of 668 bp from primer PF668;
the promoter region of 642 bp from primer PF642;
the promoter region of 622 bp from primer PF622;
the promoter region of 602 bp from primer PF602;
the promoter region of 194 bp from primer PF194; and
the promoter region of 161 bp from primer PF161;
were named pPUF819, pPUF810, pPUF779, pPUF668, pPUF642, pPUF622, pPUF602, pPUF194, and pPUF161, respectively.

(1-3) Trans formation

Five µg of each plasmid DNA prepared in (1-2) of the present example was cleaved with BamHI and subsequently transformed into Candida boidinii strain KST2515. Several colonies of the so-obtained transformants were picked up for the respective plasmids. The colonies were cultured in a medium, pH 5.5, containing 1.5% methanol, 0.67% Yeast Nitrogen Base and 0.5% yeast extract (ME media), or in a medium, pH 5.5, containing 1.0% glucose, 0.5% sodium formate and 0.67% Yeast Nitrogen Base (GF media) in order to determine an acid phosphatase activity. The acid phosphatase activity was measured by the method of Toh-e, A. et al., (J. Bacteriol., 113, 727 (1973)) using the washed-cell suspension itself as the enzyme. One unit of the enzyme activity was defined as an amount of enzyme required for generating 1 mmole of p-nitrophenol at 30° C. for one minute. According to the known literature (Sakai Y. et al., J. Bacteriol., 173, 7458 (1991)), in a transformation using URA3 as a marker, about half of the transformant cells incorporate a single copy of plasmid. Based upon this fact, the value of acid phosphatase activity with the maximal distribution of each transformant prepared with the above mentioned plasmids was regarded as a value of acid phosphatase activity of the single-copy-inserted transformant. In fact, it was confirmed by Southern analysis that a single copy of plasmid has been incorporated into each transformant. Each specific activity of acid phosphatase (unit/ $OD_{610}$) of transformants prepared with the plasmids is shown in FIG. 2 where the specific activity of acid phosphatase of pPUF1 is 100%. The results in FIG. 2 show that the specific activity is maintained at 80% or higher when the promoter region is 839 bp or larger in the case of induction with methanol, and when the promoter region is 642 bp or larger in the case of induction with formic acid.

Each specific activity is represented as a relative value to that of acid phosphatase activity of a transformant prepared with the plasmid pPUF1 with no deletion in its promoter region. The values of the parent strain were of the Candida boidinii strain KST2515 into which no plasmid has been introduced.

EXAMPLE 2

In the present example, modified FDH promoters, in which the internal region of the Candida boidinii FDH promoter has partially been deleted, were prepared and subsequently measured the activity of the acid phosphatase from Saccharomyces cerevisiae regulated by the internally-deleted-type FDH promoters to identify a region necessary for a function of the FDH promoter.

Figure 3:
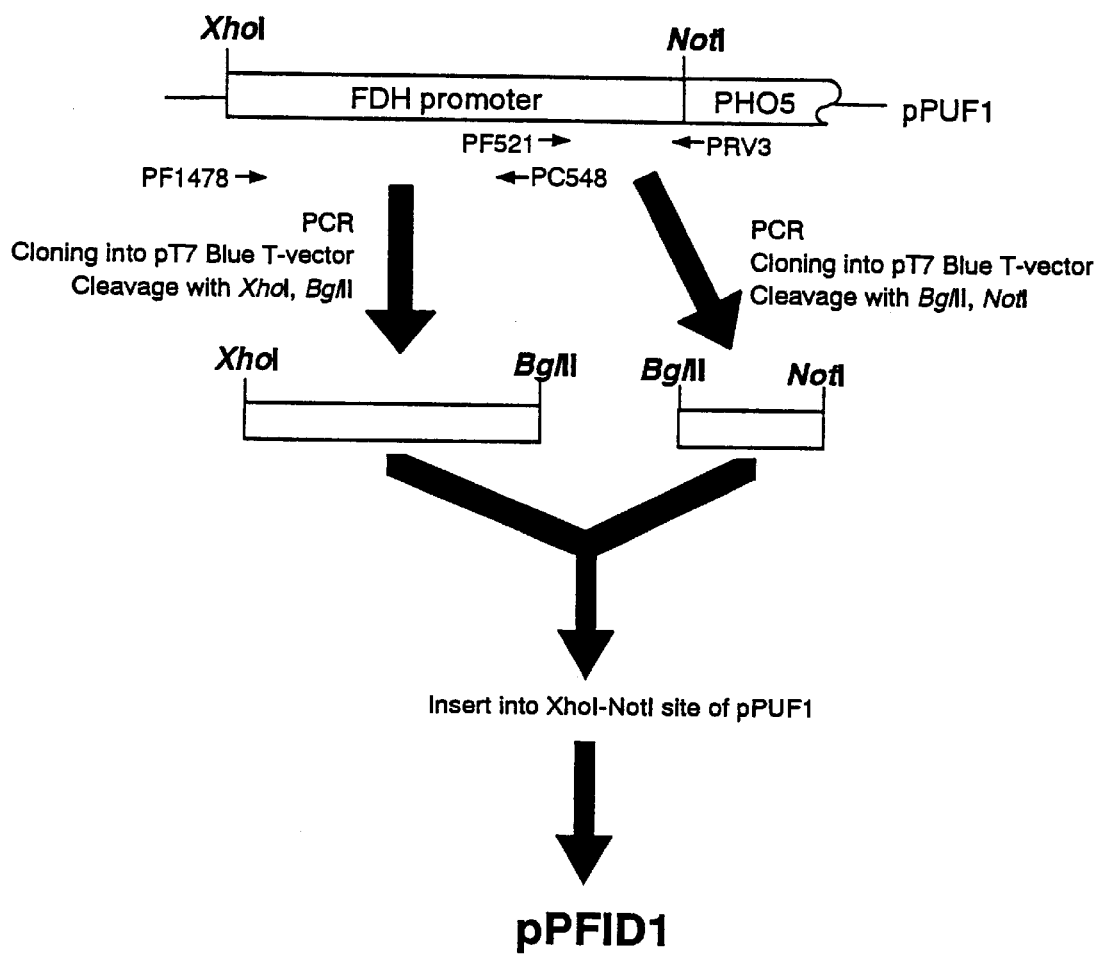
FIG. 3 shows the construction of an acid phosphatase expression plasmid pPFID1 in which an internal region of FDH promoter has been deleted.

(2-1) Construction of PHO5 Expression Plasmids Under the Control of Internally-Deleted-Type FDH Promoters Modified FDH promoters, in which the internal region of the FDH promoter has partially been deleted, were prepared by PCR (see FIG. 3 showing the construction of pPFID1). To prepare the internally-deleted-type FDH promoters by PCR, the following oligonucleotides were synthesized:

PF1478; CCCCTCGAGTCAACAAATCAATCAGC-CAATCTACC (SEQ ID NO:15)
PF521; CCAGATCTTGATAATAAGGTATACTA-CATTTTATC (SEQ ID NO:16)
PC548; CCAGATCTAGTAGTAGTGGTAGTAG-TAGTGGTAGTAGTAAGATG (SEQ ID NO:17)
PC571; CCAGATCTAGTAGTAAGATGTTACA-GATATAAAAACTACCG (SEQ ID NO:18)
PC599; CCAGATCTCTACCGTCTGATCCATG-GATTTTAATTGG (SEQ ID NO:19)
PC619; CCAGATCTTTAATTGGATAGTGGTAAA-GATATAATTATAAC (SEQ ID NO:20)
PC 641; CCAGATCTATAATTATAACATCTGAC-TAGTATTACC (SEQ ID NO:21)

Using the oligonucleotides PF521 and PRV3 together with pPUF1 as a template, PCR was conducted (20 cycles of: 94° C. for 30 sec.; 55° C. for 1 min.; and 720° C. for 1 min.). The amplified DNA fragment was cloned into pT7Blue T-Vector, from which a restriction fragment BglII-NotI was then cut out. Subsequently PCR was conducted using the oligonucleotide PF1478 and any one of the oligonucleotides PC548, PC571, PC599, PC619 and PC642 (PCR conditions: 20 cycles of: 94° C. for 30 sec.; 55° C. for 1 min.; and 72° C. for 1 min.). Each of the amplified DNA fragments was cloned into pT7Blue T-Vector, from which a restriction fragment XhoI-BglII was then cut out.

This restriction fragment was inserted into XhoI-NotI site of pPUF1 together with the above BglII-NotI DNA fragment. PHO5 expression plasmids having:

the FDH promoter fragment obtained with primer PC548, in which the nucleotides 932–957 of FDH promoter shown in SEQ ID NO:2 have been deleted; the FDH promoter fragment obtained with primer PC571, in which the nucleotides 909–957 of FDH promoter shown in SEQ ID NO:2 have been deleted;
the FDH promoter fragment obtained with primer PC599, in which nucleotides 881–957 of FDH promoter shown in SEQ ID NO:2 have been deleted;

the FDH promoter fragment obtained with primer PC619, in which nucleotides 861–957 of FDH promoter shown in SEQ ID NO:2 have been deleted; and the FDH promoter fragment obtained with primer PC642, in which the nucleotides 839–957 of FDH promoter shown in SEQ ID NO:2 have been deleted;

were named pPFID1, pPFID2, pPFID3, pPFID4 and pPFID5, respectively.

(2-2) Transformation

Figure 4:
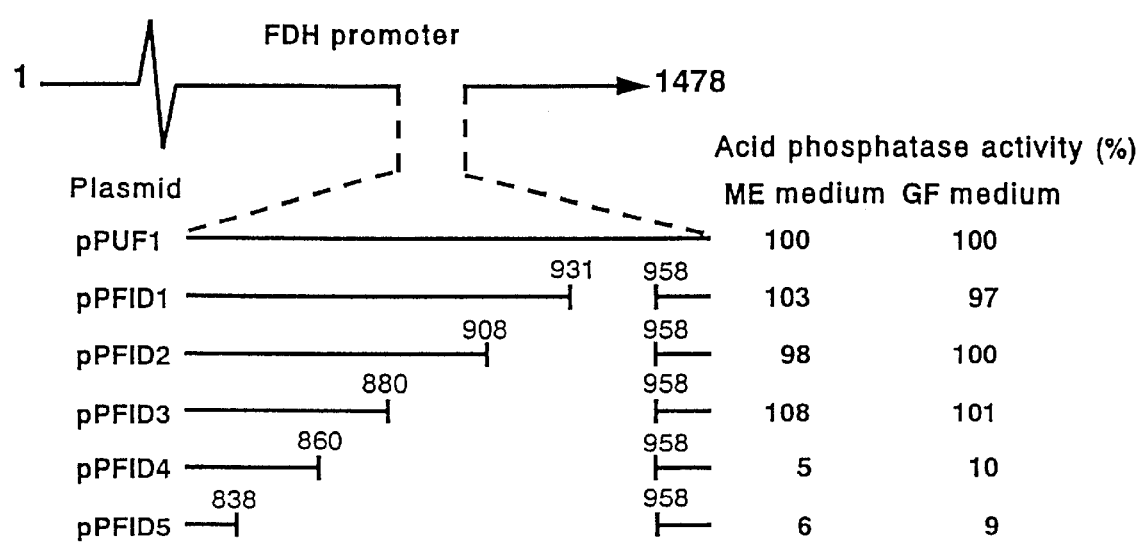
FIG. 4 shows acid phosphatase activities expressed under the control of modified FDH promoters in which the internal region of FDH promoter has partially been deleted.

The plasmids prepared in (2-1) of this example were transformed into *Candida boidinii* as described in (1-3) of Example 1 in order to determine an activity of acid phosphatase in ME and GF media. Each specific activity of acid phosphatase (unit/$OD_{610}$) of transformants prepared with the above mentioned plasmids is shown in FIG. 4, where the specific activity of acid phosphatase of pPUF1 is 100%. Each specific activity is represented as a relative value to that of acid phosphatase activity of a transformant prepared with the plasmid pPUF1 with no deletion in its promoter region.

The deletion of the nucleotides 881–957 shown in SEQ ID NO:2 did not influence the FDH promoter activity at all. However, as to a plasmid with deletion of the nucleotides 861–957, no induction of expression by methanol or formic acid was observed. From these results and the results obtained in Example 1, the nucleotide sequence 837–880 of SEQ ID NO:2 was considered to be necessary for FDH promoter activity upon induction of expression by methanol or formic acid.

EXAMPLE 3

In the present example, a *Candida boidinii* FDH promoter comprising the additional UAS sequence(s) was prepared in order to determine the activity of the acid phosphatase from Saccharomyces cerevisiae under the control of the promoter.

(3-1) Construction of PHO5 Expression Plasmid

To isolate a 1000 bp FDH promoter region having an XhoI site at the 5'end, the following oligonucleotide PXF1000 was synthesized.

PXF1000; CCCTCGAGGCTGGGTTTTTACTGAAT-TCAGTC (SEQ ID NO:22)

Using the oligonucleotides PXF1000 and PRV3 together with pPUF24 as a template, PCR was carried out (20 cycles of: 94° C. for 30 sec.; 55° C. for 1 min.; and 72° C. for 1 min.). The amplified DNA fragment was cloned into pT7 Blue T-Vector, from which a restriction fragment XhoI-NotI was cut out and subsequently inserted into XhoI-NotI of pPUF1. The thus-obtained plasmid was named pPUF24X. Oligonucleotides UA3 and UA3C, which contained the nucleotide sequence as shown in SEQ ID NO:1 that was presumed to be necessary for the FDH promoter activity based on the results from Examples 1 and 2, were synthesized.

UA3; TCGAGTTTACCACTATCCAATTAAAATC-CATGGATCAGACGGTAGCTT TACCACTATCCAAT-TAAAATCCATGGATCAGACGGTAG (SEQ ID NO:23)
UA3C; TCGACTACCGTCTGATCCATGGATTT-TAATTGGATAGTGGTAAAGCT ACCGTCTGATC-CATGGATTTTAATTGGATAGTGGTAAAC (SEQ ID NO:24)

After the synthesis, 5' ends of oligonucleotides UA3 and UA3C were phosphorylated with T4 polynucleotide kinase (Takara Shuzo Co., Ltd.). The oligonucleotides were dissolved to a final concentration of 100 pmol/µl in an annealing buffer (10 mM Tris-HCl, pH8.0, 0.1 mM EDTA, 100 mM NaCl). The solutions of the oligonucleotides UA3 and UA3C were mixed 1:1 (by volume) and heated at 95° C. for 5 minutes, and thereafter both chains were annealed while gradually cooling. Both ends of the resulting double-stranded DNA fragment enabled ligation with XhoI site. After the ligation, as shown in FIG. 5, only one end was cleaved with XhoI again.

Figure 6:
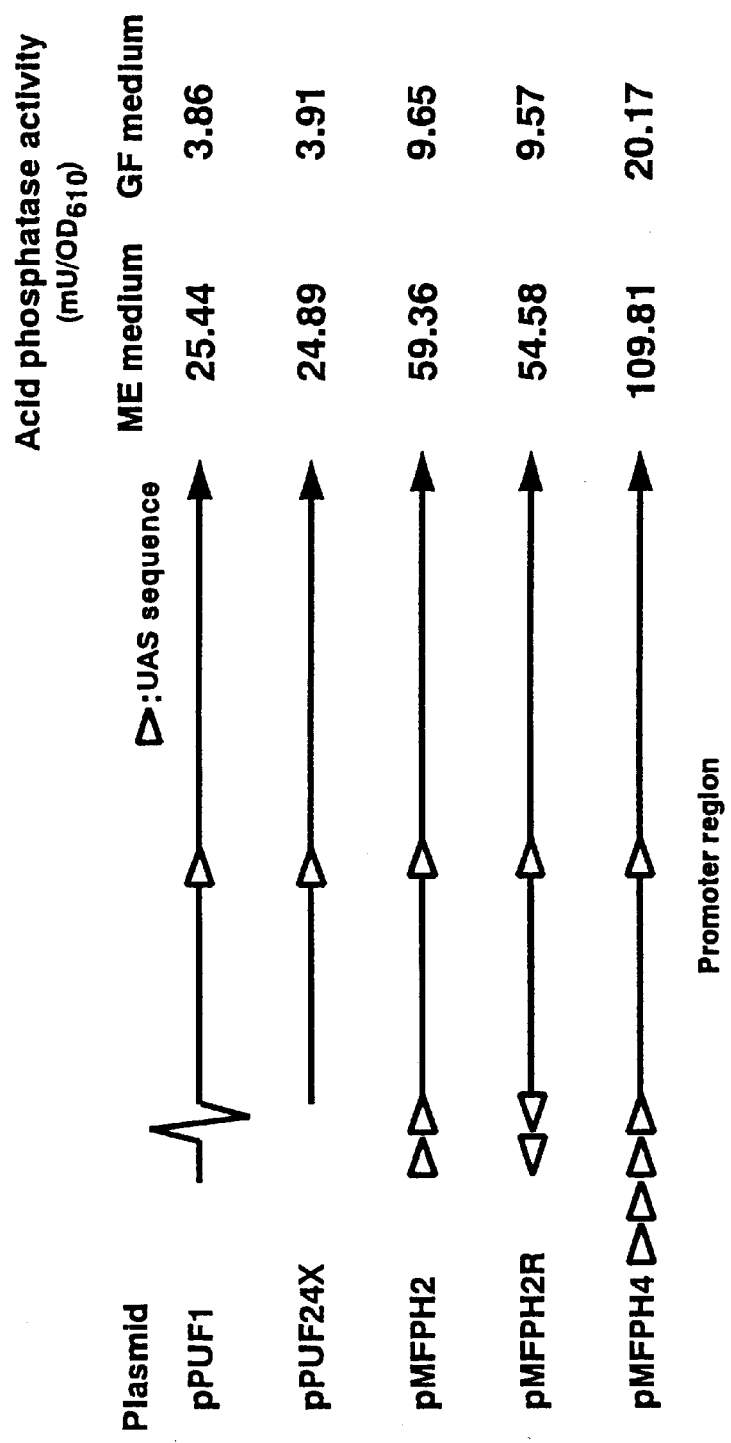
FIG. 6 shows structures of mutated FDH promoters with a sequence corresponding to SEQ ID NO:1 which is regarded as the UAS sequence, as well as acid phosphatase activities expressed under the control of the mutant FDH promoters.

Plasmid pPUF24X was cleaved with XhoI and then ligated with the above-described annealed DNA fragment. Subsequently *E. coli* DH5 was transformed with the resulting plasmid. From the several transformants plasmid DNAs were prepared and then selected for plasmids into which the synthetic DNA fragment has been inserted, by restriction enzyme analysis. The copy number and direction of the inserted DNA fragment were further determined. A plasmid inserted with 2 copies of the nucleotide sequence represented by SEQ ID NO:1 in the forward direction, a plasmid inserted with 2 copies in the reverse direction, and a plasmid inserted with 4 copies in the forward direction were named pMFPH2, pMFPH2R and pMFPH4, respectively. Each partial structure of the promoter regions of the thus-obtained plasmids is shown in FIG. 6.

(3-2) Transformation

Plasmids pMFPH2, pMFPH2R, pMFPH4 and pPUF1 prepared in (3-1) of the present example were transformed into *Candida boidinii* as described in (1-3) of Example 1 in order to measure an activity of acid phosphatase (unit/$OD_{610}$) in ME and GF media. In this measurement, 1 unit of the enzyme activity was defined as an amount of enzyme required for generating 1 mmole of p-nitrophenol at 300° C. for one minute. Each specific activity of acid phosphatase of th e single-copy-inserted transformants prepared with the above mentioned plasmids is shown in FIG. 6, where the activity is represented in $mU/OD_{601}$. The insertion of the DNA frgament resulted in the drastic increase in specific activity of acid phosphatase. This effect depended on the copy number not the direction of insertion.

From the above results, it was revealed that the inserted nucleotide sequence of SEQ ID NO:1 functioned as an UAS sequence of FDH promoter, i.e., it was a sequence necessary for inducing the FDH promoter with methanol or formic acid, and that the UAS sequence enhances a transcriptional activity of the promoter without depending on the direction of insertion.

EXAMPLE 4

In this example, a *Candida boidinii* actin gene promoter having the UAS sequence was prepared in order to determine an acid phosphatase activity of *Saccharomyces cerevisiae* under the control of the promoter.

(4-1) Construction of PHO5 Expression Plasmid

To construct the PHO5 expression plasmid comprising the actin promoter, a promoter region for *Candida boidinii* actin gene was obtained by PCR. The following oligonucleotides were synthesized based on the nucleotide sequence of the promoter region for *Candida boidinii* actin gene shown in SEQ ID NO:3:

XCAC5; TTCTCGAGTCAATAAGAGTGTGAT-TATATACAATCAGC (SEQ ID NO: 25)
NCAC3; TTGCGGCCGCTTTTGTAATATATAT-TAAATTAAATTTAT AAAATCTATC (SEQ ID NO:26)

Figure 7:
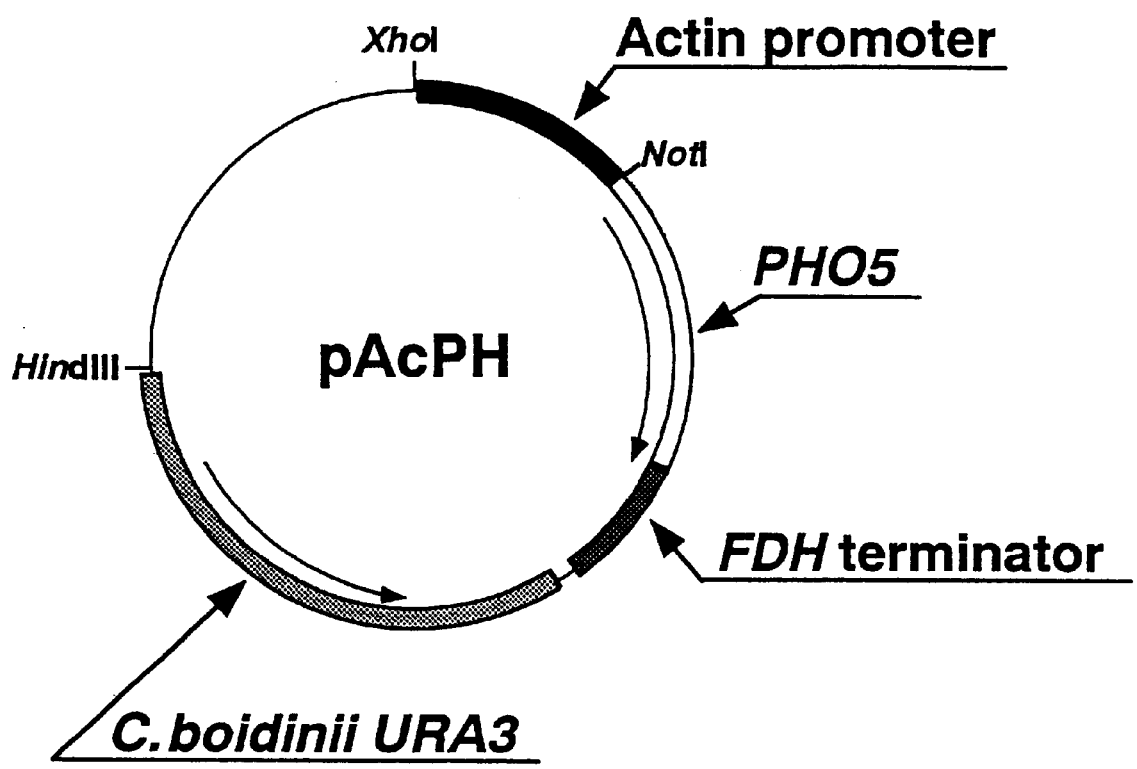
FIG. 7 shows the structure of plasmid pAcPH.

Using the oligonucleotides XCAC5 and NCAC3 together with pAcI-7 described in WO97/10345 as a temperate, PCR was carried out (20 cycles of: 94° C. for 30 sec.; 55° C. for 1 min.; and 72° C. for 1 min.). In the present example, although plasmid pAcl-7 was used as the temperate DNA of the PCR, the PCR may also be conducted using a chromosomal DNA derived from *Candida boidinii* strain ATCC 48180. After cloning the amplified DNA fragment into pT7 Blue T-Vector, a restriction fragment XhoI-NotI was cut out and subsequently inserted into XhoI-NotI site of pPUF1. The thus-obtained plasmid pAcPH (FIG. 7) was the PHO5 expression plasmid comprising an URA3 gene as a marker, the *Candida boidinii* actin gene promoter, and an FDH gene terminator.

Into the XhoI site present at the 5' end of the actin gene promoter of pACPH, a DNA fragment containing the UAS sequence was inserted in the same manner as the method described in (3-1) of Example 1. As a result, the following products were obtained: the plasmid pUAcPH2 inserted with 2 copies of UAS sequences in a forward direction; and the plasmid pUAcPH4 inserted with 4 copies of UAS sequences in a forward direction.

(4-2) Transformation

Figure 8:
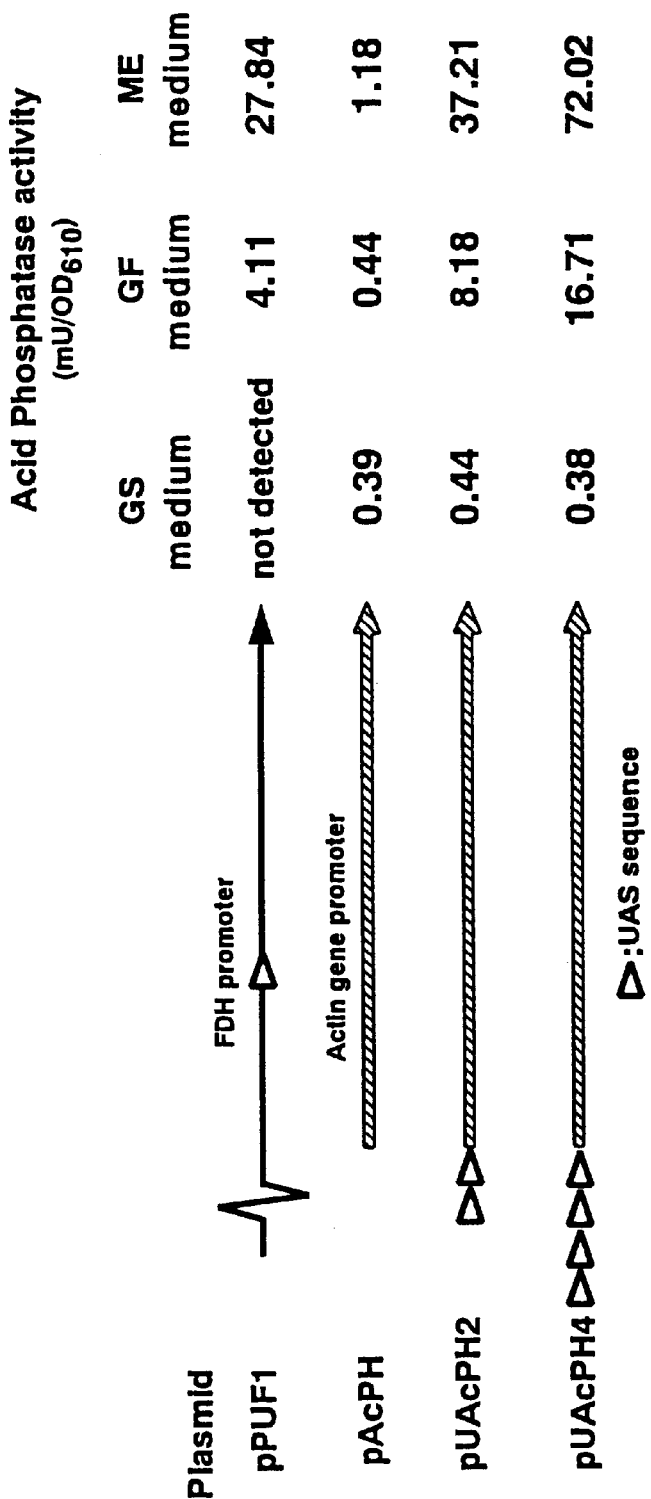
FIG. 8 shows structures of mutated actin promoters with a sequence corresponding to SEQ ID NO:1 which is regarded as the UAS sequence, as well as acid phosphatase activities expressed under the control of the mutant actin promoters.

The plasmids pAcPH, pUAcPH2, pUAcPH4 and pPUF1 prepared in (4-1) of the present example were transformed into *Candida boidinii* in the same manner as the method described in (1-3) of Example 1, except that HindIII was used for cleaving the plasmid DNA. The acid phosphatase activity of the obtained transformants was determined in ME medium, GF medium, and a medium, pH5.5, containing 1.0% glucose and 0.67% Yeast Nitrogen Base (i.e., GS medium). Each specific activity of acid phosphatase of the single-copy-inserted transformants prepared with the above mentioned plasmids is shown in FIG. 8.

In the case of the actin gene promoter without the UAS sequence (i.e., pAcPH), there was no significant difference among the acid phosphatase activities in GS, GF and ME media. In contrast, the actin gene promoters with the UAS sequence (i.e., pUAcPH2 and pUAcPH4) showed a remarkable increase in the activity in the GF and ME media, the result being similar to the case of the promoter for formate dehydrogenase gene.

The above-described results showed that the UAS sequence described in Example 3 had the effect of enhancing not only the activity of the FDH promoter but also activities of other promoters.

INDUSTRIAL APPLICABILITY

According to the present invention, there are provided a promoter with a high transcriptional activity, an expression vector carrying the promoter, a transformant introduced with the expression vector, a method for enhancing the promoter activity, and a method for producing heterologous proteins. The mutant promoter according to the present invention has a remarkably enhanced promoter activity compared with that of a wild type promoter. Thus, it is highly valuable as a promoter for expressing heterologous genes. The expression vector of the present invention is capable of efficiently expressing and producing various useful proteins.

SEQUENCE LISTING FREE TEXT

SEQ ID NO. 1: Synthetic DNA
SEQ ID NO. 4: Synthetic DNA
SEQ ID NO. 5: Synthetic DNA
SEQ ID NO. 6: Synthetic DNA
SEQ ID NO. 7: Synthetic DNA
SEQ ID NO. 8: Synthetic DNA
SEQ ID NO. 9: Synthetic DNA
SEQ ID NO. 10: Synthetic DNA
SEQ ID NO. 11: Synthetic DNA
SEQ ID NO. 12: Synthetic DNA
SEQ ID NO. 13: Synthetic DNA
SEQ ID NO. 14: Synthetic DNA
SEQ ID NO. 15: Synthetic DNA
SEQ ID NO. 16: Synthetic DNA
SEQ ID NO. 17: Synthetic DNA
SEQ ID NO. 18: Synthetic DNA
SEQ ID NO. 19: Synthetic DNA
SEQ ID NO. 20: Synthetic DNA
SEQ ID NO. 21: Synthetic DNA
SEQ ID NO. 22: Synthetic DNA
SEQ ID NO. 23: Synthetic DNA
SEQ ID NO. 24: Synthetic DNA
SEQ ID NO. 25: Synthetic DNA
SEQ ID NO. 26: Synthetic DNA

What is claimed is:

1. An isolated DNA molecule consisting of the sequence of SEQ ID NO: 1 or SEQ ID NO: 4.

2. A polynucleotide molecule comprising, (A) a promoter functionally linked to (B) a DNA segment having the sequence of SEQ ID NO: 1 or SEQ ID NO: 4.

3. The polynucleotide of claim 2, wherein said polynucleotide comprises two or more copies of SEQ ID NO: 1 or SEQ ID NO: 4.

4. A mutant promoter comprising a DNA molecule having the sequence of SEQ ID NO: 1 or SEQ ID NO: 4.

5. The mutant promoter of claim 4, wherein said mutant promoter comprises two or more copies of SEQ ID NO: 1 or SEQ ID NO: 4.

6. A recombinant expression vector comprising the mutant promoter of claim 4 operably linked to a heterologous gene.

7. A recombinant expression vector comprising the polynucleotide of claim 2 operably linked to a heterologous gene.

8. A yeast transformed with the recombinant expression vector of claim 6.

9. A yeast transformed with the recombinant expression vector of claim 7.

10. A process for preparing an expression product of a heterologous gene comprising:
   (1) transforming a yeast with the recombinant expression vector of claim 6;
   (2) culturing the transformed yeast in the presence of a sufficient amount of methanol or formic acid to induce expression of the heterologous gene, thereby allowing the heterologous gene to express; and
   (3) isolating the expression product of the heterologous gene.

11. A process for preparing an expression product of a heterologous gene comprising:
   (1) transforming a yeast with the recombinant expression vector of claim 7;
   (2) culturing the transformed yeast in the presence of a sufficient amount of methanol or formic acid to induce expression of the heterologous gene, thereby allowing the heterologous gene to express; and
   (3) isolating the expression product of the heterologous gene.

* * * * *